United States Patent [19]

Cecco et al.

[11] Patent Number: 4,808,927
[45] Date of Patent: Feb. 28, 1989

[54] CIRCUMFERENTIALLY COMPENSATING EDDY CURRENT PROBE WITH ALTERNATELY POLARIZED RECEIVER COIL

[75] Inventors: Valentino S. Cecco; Richard McIlquham; F. Leonard Sharp, all of Deep River, Canada

[73] Assignee: Atomic Energy of Canada Limited, Ottawa, Canada

[21] Appl. No.: 16,748

[22] Filed: Feb. 19, 1987

[51] Int. Cl.⁴ .................... G01N 27/90; G01R 33/12
[52] U.S. Cl. ................................ 324/220; 324/225; 324/232; 324/242
[58] Field of Search ................ 324/219–221, 324/225, 232, 240–243

[56] References Cited

U.S. PATENT DOCUMENTS

| | | | |
|---|---|---|---|
| 2,124,579 | 7/1938 | Knerr et al. | 324/242 X |
| 2,467,306 | 4/1949 | Habig | 324/242 |
| 2,746,012 | 5/1956 | Price | 324/242 |
| 3,166,710 | 1/1965 | Schmidt | 324/242 |
| 3,202,914 | 8/1965 | Deem et al. | 324/242 |
| 3,241,058 | 5/1966 | Quittner | 324/242 |
| 3,271,662 | 9/1966 | Quittner | 324/233 |
| 3,284,701 | 11/1966 | Kerbow | 324/221 X |
| 3,444,459 | 5/1969 | Prindle et al. | 324/242 |
| 3,617,874 | 11/1971 | Forster | 324/241 |
| 3,694,740 | 9/1972 | Bergstrand | 324/240 X |
| 3,944,911 | 3/1976 | Tornblom | 324/242 |
| 3,952,315 | 4/1976 | Cecco | 324/220 |
| 4,079,312 | 3/1978 | Osborn et al. | 324/225 X |
| 4,083,002 | 4/1978 | Allport | 324/232 X |
| 4,608,534 | 8/1986 | Cecco et al. | 324/220 X |
| 4,649,343 | 3/1987 | Birchak et al. | 324/220 |
| 4,742,298 | 5/1988 | Ando et al. | 324/220 |

FOREIGN PATENT DOCUMENTS 0065325 11/1982 European Pat. Off. ............ 324/220

*Primary Examiner*—Gerard R. Strecker
*Attorney, Agent, or Firm*—Yoshiharu Toyooka

[57] ABSTRACT

An eddy current probe capable of detecting localized defects with 100% circumferential coverage in tubes, tubes under support plates etc., is disclosed. The probe employs multiple receiver coils with each excitation coil, operating in transmit-receive mode in which alternate receiver coils are electromagnetically polarized in opposite directions. The probe detects localized defects and eliminates concentric variations.

4 Claims, 4 Drawing Sheets

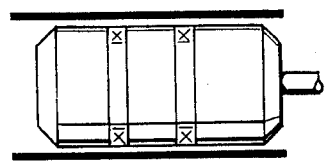
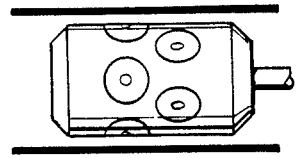
FIG. 1a PRIOR ART
FIG. 1b PRIOR ART
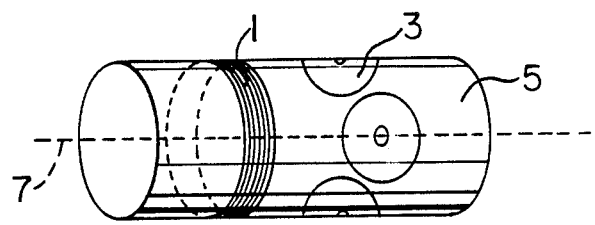
FIG. 2
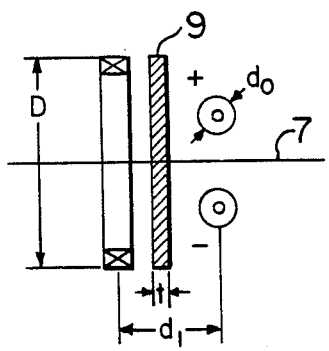
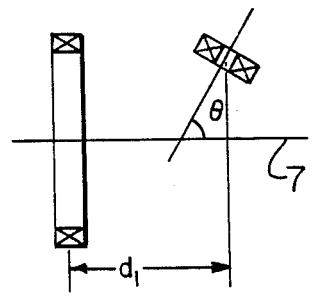
FIG. 3a
FIG. 3b

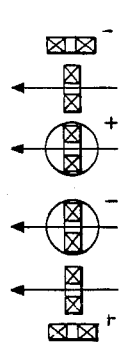
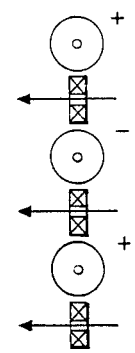
FIG. 4a        FIG. 4b
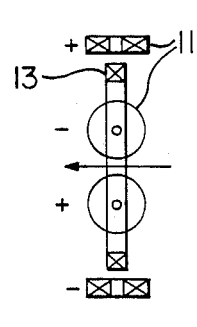
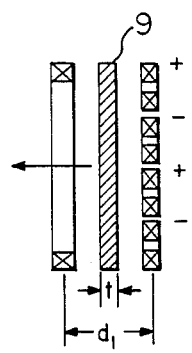
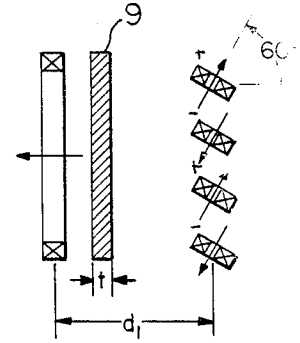
FIG. 5        FIG. 6        FIG. 7

CIRCUMFERENTIALLY COMPENSATING EDDY CURRENT PROBE WITH ALTERNATELY POLARIZED RECEIVER COIL

This invention relates to the non-destructive testing of a tube made of a non-ferromagnetic and electrically conductive material and in particular to an eddy current probe having an excitation coil and multiple receiver coils. The probe according to the present invention is capable of detecting, in a tube, both circumferential and axial cracks, fretting wear, shallow defects, etc., under ferromagnetic and non-ferromagnetic support plates. Therefore, in conventional eddy current probes, factors causing circumferential structural variations such as support plates, tubesheets, etc., about a tube under inspection, changes in tube diameter, etc., introduce marked deviation in output signals, thus making the detection of defects very difficult, if not impossible. In the present eddy current probes, however, these circumferential variations are made invisible (compensated) in the output. Thus, it is decided that "circumferentially compensated", "circumferentially compensating", "tubesheet compensating" or such terms are used to denote this ability throughout the present specification and claims.

BACKGROUND OF THE INVENTION

Eddy current testing is a non-destructive test technique based on inducing electrical currents in the material being inspected and observing the interaction between these currents and the material. Eddy currents are generated by electromagnetic coils in the test probe, and monitored simultaneously by measuring probe electrical impedance. Since it is an electromagnetic induction process, direct electrical contact with the sample is not required; however, the sample material must be electrically conductive.

When inspecting for defects, it is essential that flow of eddy currents be as perpendicular as possible to defects to obtain maximum response. If eddy currents flow parallel to a defect, there will be little distortion of the eddy currents and hence little change in probe impedance.

Various eddy current probes have been proposed for inspecting cylindrical or tubular components as seen in U.S. Pat. Nos. 3,952,315 Apr. 20, 1976 (Cecco), 4,079,312 Mar. 14, 1978 (Osborne et al) and 4,083,002 Apr. 4, 1978 (Allport).

A conventional internal circumferential probe induces a flow of eddy currents parallel to the coil windings and therefore circumferential in direction. As mentioned above, coil impedance must change to sense a defect. This will occur if eddy current flow path is disturbed. Circumferential defects parallel to this current, which present no significant area perpendicular to this path, will therefore not be sensed. Multiple coils in excitation coil assembly and in receiver coil assembly are also described in U.S. Pat. Nos. 3,241,058 Mar. 15, 1966 (Quittner) and 3,271,662 Sept. 6, 1966 (Quittner). The above two patents to Quittner teach sheet metal inspection using an odd number of coils with their axes perpendicular to test sample for excitation and an even number of coils for receiving. The excitation coils are electromagnetically polarized alternately but the receiver coils are polarized in same directions and therefore no circumferential or line compensation is possible (a desired feature in the Quittner patent). They also produce complicated output signals to analyze and are not readily applicable for cylindrical testing.

U.S. Pat. No. 3,444,459, May 13, 1969 (Prindle et al) describes helical sensing coils slightly skewed relative to the axis of the tube. The sensing coils are alternately polarized but must be in an elongated shape for 100% circumferential coverage and manageable axial probe length. The excitation coil is at least three times larger than the sensing coil coil assembly. The probe has no sensitivity to circumferential cracks.

The present invention makes use of an excitation coil for each set of multiple receiver coils operating in the transmit-receive mode for detecting defects in a cylindrical tube.

THE OBJECTS OF THE PRESENT INVENTION

It is an object of the present invention to provide an eddy current probe which is sensitive to localized defects in a cylindrical tube.

It is another object of the present invention to provide an eddy current probe which produces circumferentially compensated output signal.

It is a further object of the present invention to provide an eddy current probe which can detect defects in a tube under tubesheet or supports.

It is a still further object of the present invention to provide an eddy current probe which produces outputs similar in nature to those of conventional probes for ease of analyses.

SUMMARY OF THE INVENTION

Briefly stated, a circumferentially compensating eddy current probe of the present invention includes a first coil assembly and a second coil assembly. The first coil assembly has a first coil arrayed in a first plane perpendicular to the central axis of a tube under inspection to be located adjacent to the tube. The first coil has an axis parallel to the central axis to generate magnetic fields in the tube in the direction of the central axis. The second coil assembly has an even number of substantially identical coils to be located adjacent to the tube and symmetrically about and in a second plane perpendicular to the central axis. The second coils have axes which form an angle $\theta$ with the central axis and are electromagnetically polarized alternately along their axes. The second coil assembly senses distortions in the magnetic fields and produces a circumferentially compensated output indicating essentially the presence of localized flaws in the tube.

BRIEF DESCRIPTION OF THE DRAWINGS

In a more complete understanding of the present invention and for further objects and advantages thereof, references may be made to the following description taken in conjunction with the accompanying drawings in which:

FIGS. 1(a) and 1(b) illustrate perspective views of two prior art devices without circumferential compensation.

FIG. 2 shows a probe in perspective view according to one preferred embodiment of the invention.

FIGS. 3(a) and 3(b) are generalized planar views of the present invention indicating symbols for various parameters.

FIGS. 4(a) and 4(b) are planar views of two preferred embodiments of the present invention.

FIGS. 5, 6 and 7 are planar views of other preferred embodiments of the invention.

DETAILED DESCRIPTION OF PREFERRED EMBODIMENT

To detect defects the coil must induce currents at an angle to the defect plane. FIGS. 1(a) and 1(b) show two possible types of probes. Neither has separate excitation and receiver coil assemblies. The probe in FIG. 1(a) induces currents in a circular pattern whereas the probe in FIG. 1(b) induces currents flow circumferentially. Both probes are of differential type in that the coils are electrically connected to generate differential signals using an ac bridge. While pancake type surface probes (single or multiple) have good sensitivity to surface cracks, they have low sensitivity to external defects, large lift-off noise and yield complex signals. In addition, the complex mechanical design required to minimize lift-off noise makes the probe prone to failure.

For detecting defects under tubesheets and in transition regions of finned tubes etc, dual or multi-frequency eddy current methods are known. High test frequencies are very sensitive to tube expansion, low test frequencies are very sensitive to tube sheet and support plates, while intermediate ones are sensitive to defects, support plates and expansions. A proper mix of these multifrequency signals results in sensitivity primarily to defects.

Tubesheet compensating probes, according to the present invention are designed to simplify eddy current testing. Defects close to or under a tubesheet or support plates can be detected without using multifrequency compensation (mixing of signals) or small surface probes. These probes of the present invention, operating on conventional transmit-receive eddy current instruments, have built-in circumferential compensation such that support plates, tubesheets and expanded section are virtually invisible. A complete tube inspection yields signals only from defects. They can be used to detect stress-corrosion cracks, fatigue cracks, pits even in the presence of uniform copper deposits, and fretting wear under support plates. Inconel (Trade Mark) steam generator tubes, brass condenser tubes and copper finned air conditioner heat exchanger tubes can be inspected with a single scan using a single frequency transmit-receive eddy current instrument.

Figures 8, 9:
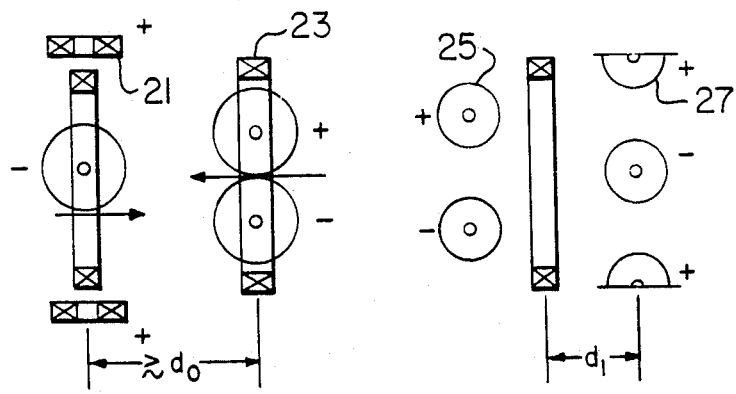
FIGS. 8, 9 and 10 are planar views of variations of the preferred embodiments of the invention facilitating a 100% circumferential coverage.

This probe is "user-friendly" since it gives the familiar "figure-8" signals typical of standard differential probes. It is almost completely insensitive to probe-wobble noise and can provide 100% circumferential coverage.

FIG. 2 shows perspectively a coil configuration according to one preferred embodiment of the present invention. In the figure a first coil assembly 1 and a second coil assembly 3 are provided on a probe housing 5 which is to be moved inside and along the central axis 7 of a tube under inspection. In this embodiment, the first coil assembly is made of a coil of "the bobbin type" wound about the probe housing in a first plane. When the probe is inserted in the tube the coil of the first coil assembly is concentrically positioned in the proximity of the inner surface of the tube. The coil has an axis coinciding substantially with the central axis 7 of the tube so that the first plane is perpendicular to the central axis. The second coil assembly 3 has four substantially identical second coils of a so called "pancake" type. The identical second coils are located 90° apart in a circle about the tube and their axes radiate from the central axis in a second plane perpendicular thereto. The first coil assembly is connected to a ac power source to generate a magnetic field in an axial direction and the second coil assembly to a voltage measuring instrument which produces a circumferentially compensated output.

The bobbin coil of the first coil assembly generates a magnetic field of substantially a toroidal shape about the tube. The flux lines within the coil are parallel to the central axis 7, thus containing no radial components. However, the flux lines outside the coil possess axial as well as radial components, as they deviate away from the central axis. The second coil assembly is located where the flux lines contain radial and axial components so that they detect magnetic distortions in all directions.

A variety of coil configurations are possible and will be discussed in general terms below by referring to FIGS. 3(a) and 3(b). In FIG. 3(a), there is depicted a coil configuration having one bobbin coil in the first coil assembly and four second coils (only two being shown) in the second coil assembly. The second coils are positioned symmetrically in a circle in a second plane. Several symbols are included to indicate certain variable parameters e.g. $d_1$, the distance between the coil assemblies, that is, between the two perpendicular planes, D and $d_0$, the diameters of the first and the second coils respectively and t the thickness of a partial shield 9 which will be described below. In FIG. 3(b) another embodiment is shown wherein the second coils are positioned at an angle $\theta$ with the central axis 7 (only one second coil being shown in the figure).

These parameters $d_0$, $d_1$, t and $\theta$ are variable and can be chosen to optimize the performance to suit the requirements. The sensitivity can be maximized by making the bobbin coil width about equal to the tube thickness. The number of coils in a coil assembly can also be chosen among the even numbers.

In FIG. 3(a) and figures which will follow, the signs + and − indicate the polarities of the coils which can be determined by either the direction of coil windings or by electrical connections in series, parallel or both among the coils. However the polarity among the second coils, regardless of the second number of the coils, must always be alternating.

For each of the coil numbers, e.g. 2, 4, 6 . . . , the following coil configurations are possible.

(1) $\theta = 90°, 270°$ alternating, $d_1 = 0$
(2) $\theta = 0°, 180°$ alternating, $d_1 = 0$
(3) $\theta = 90°, 270°$ alternating, $d_1 \geq d_0$
(4) $\theta = 0°, 180°$ alternating, $d_1 \geq d_0$
(5) $\theta = 90°, 270°$ alternating, $d_1 \geq d_0 + t$, $t \approx \delta$
(6) $\theta = 0°, 180°$ alternating, $d_1 \geq d_0 + t$, $t \approx \delta$
(7) $\theta = 90°, 270°$ alternating, $d_1 \approx 2D$
(8) $\theta = 0°, 180°$ alternating, $d_1 \approx 2D$
(9) $\theta \approx 30° - 60°, 210° - 240°$ alternating, $d_1 \geq 2d_0$
(10) $\theta \approx 30° - 60°, 210° - 240°$ alternating, $d_1 \geq 2d_0 + t$, $t \approx \delta$
(11) $\theta \approx 30° - 60°, 210° - 240°$ alternating, $d_1 \approx 2D$ In the above listing, $\delta$ is the standard depth of penetration governed by the test frequency, electrical conductivity and the magnetic permeability of the partial shield.

FIGS. 4(a) and 4(b) show two other embodiments which are similar to Case No. 1 above but instead of a single bobbin coil, in the embodiment the first coil assembly is made up of the same even number of identical first coils, all being aligned axially but polarized in a same direction as shown by arrows. The first coils can be connected in series, parallel or both with each other, as long as they are polarized in a same direction. The first and the second coils are arranged in one plane, e.g. $d_1=0$. While both coils are positioned at the same circumferential locations in FIG. 4(a), in FIG. 4(b) they are angularly displaced from each other so that each first coil is at midpoint of two adjacent second coils. To aid in visualizing certain coil configuration listed above, reference may be made to FIGS. 5, 6, and 7.

In FIG. 5, an embodiment under coil configuration Case No. 1 above is shown in that six second coils 11 (only four shown) are symmetrically positioned at 60° apart in the same plane as the first coil 13. The polarities are alternated among the second coils, thus $\theta$ being 90° and 270°. In FIG. 6, the first coil and six second coils (four shown) are spaced apart by a distance of $d_1 \geq d_0 + t$. This embodiment comes under Case No. 6 and has a partial shield 9 of copper to rotate the phase of the defect signal relative to probe wobble signal. The polarity of the first coils is shown by an arrow and those of the second coils are indicated by + and − in those figures. In FIG. 6, $\theta$, therefore, is alternating between 0° and 180°.

FIG. 7 shows an embodiment which is listed under Case No. 10 in that $\theta$ is taken alternately between 60° and 210°. These angles minimize direct coupling of the first coil assembly and the second coil assembly but maximize sensitivity to external defects. The embodiment further minimizes probe wobble signal and also distorts localized defect signals so that they become more distinguishable from the probe wobble noise.

All the coil configurations so far discussed have certain areas of circumference undetected, e.g. small areas that pass right under the centers of the coils. However, a 100% circumferential coverage can be obtained by providing additional set of coil assemblies.

Figure 10:
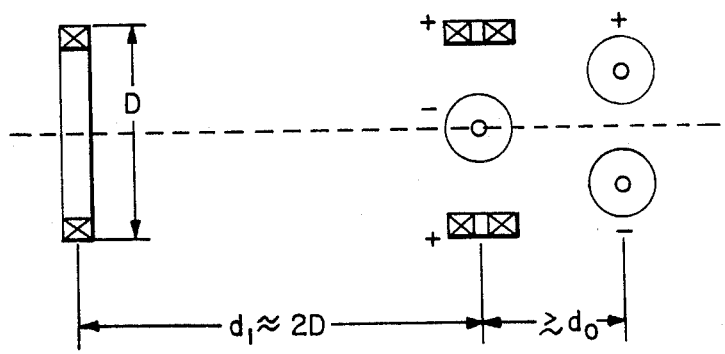

FIGS. 8, 9 and 10, therefore, illustrate a few typical coil configurations according to the present invention.

In FIG. 8, two identical sets 21 and 23 of coil configuration of No 1 each having one first coil and four identical second coils. The sets are spaced apart from each other by a distance of at least $d_0$ and are angularly rotated from each other by 45°.

Figure 11:
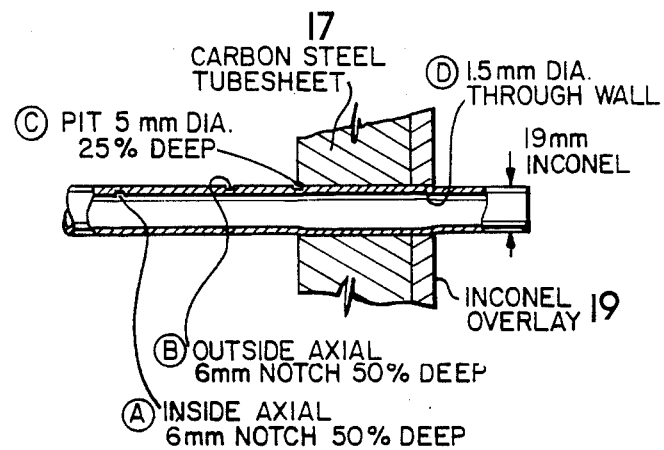
FIG. 11 is a steam generator tube mock-up used for testing of the probes of the present invention.
Figure 12:
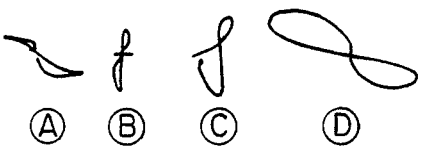
FIG. 12 shows output signals obtained in a test conducted on the mock-up of FIG. 11.

FIGS. 11 and 12 show a steam generator mock-up having various types of defects and output signals obtained by a probe constructed according to the present invention as shown in FIG. 8. In FIG. 11, the tube made of Inconel (Trade Mark) is shown to have a diameter of 19 mm. Various defects are shown at locations A, B, C and D. The tubesheet 17 is carbon steel and an Inconel (Trade Mark) overlay is at 19.

FIG. 12 illustrates output signals in X-Y impedance pattern obtained at locations A, B, C and D. The through-wall hole and 25% deep, 5 mm diameter external pit are readily detectable at the tubesheet expansion transition. The undistorted signals permit accurate defect sizing. The signals from the carbon steel tubesheet, Inconel (Trade Mark) overlay and tubesheet expansion are negligible.

Referring back to FIGS. 9 and 10, other embodiments for 100% coverage are shown. In FIG. 9, one first coil is positioned at midpoint between two sets 25 and 27 of four second coils. This is a variation of the configuration Case No. 3, thus the distance between the first and the second coils is at least $d_0$. The two sets are angularly displaced from each other by 45°. FIG. 10 describes another embodiment which includes two sets of four second coils each, being positioned on one side of the first coil at a distance of about 2D. The distance between the two sets is at least $d_0$.

As can be easily visualized, all the coil configurations can be implemented by an internal probe as well as by an external probe in that the coils can be positioned on one side of the tube, inside or outside with no changes in characteristics.

Figure 13:
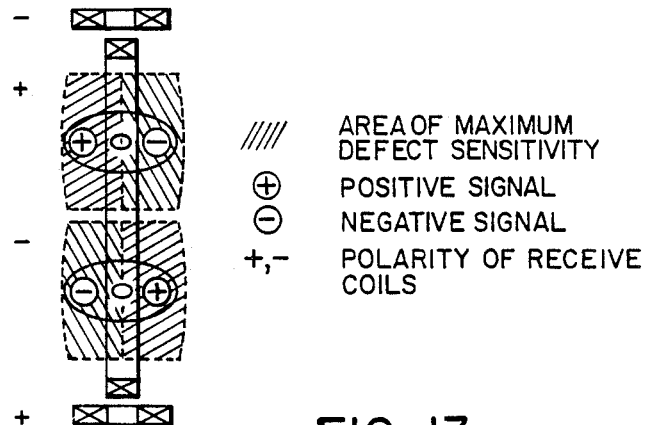
FIG. 13 is a simplified planar view according to one of the embodiments of the present invention, showing areas of detection.

FIG. 13 illustrate a planar view of coil configuration Case No. 1. As seen in the figure, the receive coils are pancake coils and have the diameter larger than the width of the transmit coil, thus ensuring that the receive coils are positioned where the toroidal magnetic field has the radial and axial components. In the figure, there are also indicated + and −, which mean that the receive coils (second coils) produce positive signal and negative signal respectively in response to distortions in the magnetic field in these areas. Areas of maximum defect sensitivity and polarities of the second coils are also indicated. Thus the alternative polarization of the receive coils achieves circumferential compensation and their symmetrical large diameters produce axial differentiation of signals so that good defect detectability under minimum noise of the probe is realized.

In connection with FIG. 11 in particular but applicable to all other embodiments of the present invention, the following observations can be made:

Transmit (first) coils.
  axially oriented.
Receive (second) coils
  Coils connected with alternating N-S, S-N polarities result in:
  High defect sensitivity areas under and between coils;
  Each adjacent coil has alternating positive and negative sensitivity;
  When $d_1=0$ such as one shown in FIG. 11, defect sensitivity areas alternate in signal polarity, e.g. plus-minus for one coil and minus-plus for adjacent coil; and
  This alternating defect sensitivity around tube circumference results in cancellation of signals from symmetrical variations such as support plates, tubesheets, expansion areas etc.
Resultant signal from localized defects is similar to conventional differential probes, thus facilitating signal analyses. This allows defect sizing even under support plates or tube expansion regions.

We claim:
1. A circumferentially compensating eddy current probe for detecting localized flaws in a tube having a central axis and made of an electrically conductive material, while compensating for circumferential structural variations therein, comprising:
  a first coil assembly and a second coil assembly to be located inside the tube under inspection;
  the said first coil assembly having at least one first coil arranged in a plane perpendicular to the central axis and to be located adjacent to the tube under inspection, the at least one first coil having an axis parallel to the central axis to generate at least one magnetic field of a substantially toroidal shape in and through the tube in the direction of the central axis;

the said second coil assembly having an even number of substantially identical second coils to be located between the said first coil assembly and the tube under inspection and symmetrically thereabout and in the said plane perpendicular to the central axis in the said magnetic field of the toroidal shape where radial and axial components of the said magnetic field exist, the said second coils having diameters larger than the width of the first coil and having axes perpendicular to the said central axis and being electromagnetically polarized alternately along their axes so that the second coil assembly senses distortions in the magnetic fields and produces a circumferentially compensated output indicating essentially the presence of localized flaws in the tube.

2. The eddy current probe according to claim 1 wherein:

the first coil assembly comprises the same even number of substantially identical first coils as that of the second coils;

the said first coils being arranged symmetrically about the central axis in the first plane and having axes parallel to the central axis to generate magnetic fields of a substantially toroidal shape in and through the tube in the direction of the central axis.

3. The eddy current probe according to claim 1 wherein:

the said even number of the second coils is a number selected from a group consisting of 2, 4 and 6; and the first and the second coil assemblies are provided on a probe housing to be freely movable along the central axis inside the tube.

4. The eddy current probe according to claim 3, further comprising:

an additional set of third and fourth coil assemblies, both located axially adjacent to the set of the first and second coil assemblies;

the said third coil assembly having a third coil and being identical to the first coil assembly;

the said fourth coil assembly having fourth coils and being identical to the second coil assembly; wherein the said even number of the second and the fourth coils is 4; and the set of the first and the second coil assemblies is angularly displaced by 45° about the central axis and axially displaced by a distance of at least $d_0$ from the said additional set, $d_0$ being the diameter of the second coil.

* * * * *